United States Patent [19]

Scher et al.

[11] Patent Number: 4,956,129
[45] Date of Patent: Sep. 11, 1990

[54] MICROENCAPSULATION PROCESS

[75] Inventors: Herbert B. Scher, Moraga; Marius Rodson, El Cerrito, both of Calif.

[73] Assignee: ICI Americas Inc., Wilmington, Del.

[21] Appl. No.: 151,048

[22] Filed: Feb. 1, 1988

Related U.S. Application Data

[63] Continuation-in-part of Ser. No. 595,136, Mar. 30, 1984, abandoned, which is a continuation-in-part of Ser. No. 499,973, Jun. 1, 1983, abandoned, which is a continuation-in-part of Ser. No. 201,686, Oct. 30, 1980, abandoned.

[51] Int. Cl.$^5$ .................. A61K 9/50; A61K 9/52; B01J 13/02
[52] U.S. Cl. .................. 264/4.7; 71/DIG. 1; 264/4.3; 264/4.33; 424/406; 424/408; 424/457; 424/497; 424/402.21; 514/963
[58] Field of Search .................. 264/4.3, 4.33, 4.7; 428/402.21; 424/408, 457, 497; 514/963

[56] References Cited

U.S. PATENT DOCUMENTS

| | | | |
|---|---|---|---|
| 3,016,308 | 1/1962 | Macaulay | 264/46 X |
| 3,074,845 | 1/1963 | Geary | 424/419 |
| 3,137,631 | 6/1964 | Soloway | 424/494 |
| 3,516,941 | 6/1970 | Matson | 264/4.7 X |
| 3,686,015 | 8/1972 | Powell et al. | 264/4.3 X |
| 4,001,140 | 1/1977 | Foris et al. | 264/4.7 |
| 4,073,968 | 2/1978 | Miyamoto et al. | 430/138 X |
| 4,157,983 | 6/1979 | Golden | 264/4.7 X |
| 4,223,060 | 9/1980 | Raine et al. | 428/402.21 X |
| 4,576,891 | 3/1986 | Adair et al. | 428/402.21 X |

OTHER PUBLICATIONS

Nygen et al.: *Modern Surface Coatings*, Interscience Publishers, N.Y., (1965), pp. 190–193.

*Primary Examiner*—Richard D. Lovering
*Attorney, Agent, or Firm*—Denis A. Polyn

[57] ABSTRACT

A process is disclosed for the microencapsulation of a substantially water-insoluble liquid material within a porous shell to effect a slow rate of release of said material through said shell which comprises (a) providing an organic solution comprising said material and an etherified urea-formaldehyde prepolymer dissolved therein which from about 50% to about 98% of the methylol groups of said prepolymer have been etherified with a $C_4$-$C_{10}$ alcohol; (b) creating an emulsion of said organic solution in an continuous phase aqueous solution comprising water and a surfaceactive agent, wherein said emulsion comprises discrete droplets of said organic solution dispersed in said continuous phase aqueous solution, there being formed thereby an interface between the discrete droplets of organic solution and the surrounding continuous phase aqueous solution; and (c) causing in situ self-condensation and curing of said urea-formaldehyde prepolymers in the organic phase of said discrete droplets adjacent to said interface by simultaneously heating said emulsion to a temperature between about 20° C. to about 100° C., and adding to said emulsion an acidifying agent and maintaining said emulsion at a pH of between about 0 to about 4 for a sufficient period of time to allow substantial completion of in situ condensation of said resin prepolymers to convert the liquid droplets of said organic solution to capsules consisting of solid permeable polymer shells enclosing said liquid material.

Also disclosed are the microcapsules formed by the above-described process.

18 Claims, No Drawings

MICROENCAPSULATION PROCESS

CROSS REFERENCE TO RELATED APPLICATIONS

This application is a continuation-in-part of application Ser. No. 595,136, filed Mar. 30, 1984 and now abandoned; which in turn is a continuation-in-part application of Ser. No. 499,973, filed June 1, 1983, now abandoned; which in turn is a continuation-in-part of application Ser. No. 201,686, filed Oct. 30, 1980, now abandoned.

BACKGROUND OF THE INVENTION

A. Field of the Invention

This invention relates to microcapsules and to a process for their production. In particular, this invention relates to encapsulated droplets of a liquid material which is substantially insoluble in water, where the encapsulating agent is a film formed from a modified urea-formaldehyde polymer.

B. Description of the Prior Art

The use of membranes, coatings, and capsules for the controlled release of liquid materials is well known in the art of both agricultural and non agricultural chemicals. In agriculture, controlled-release techniques have improved the efficiency of herbicides, insecticides, fungicides, bactericides, and fertilizers. Non-agricultural uses include encapsulated dyes, inks, pharmaceuticals, flavoring agents, and fragrances.

The most common forms of controlled-release materials are coated droplets or microcapsules, coated solids including both porous and non-porous particles, and coated aggregates of solid particles. In some instances, a water-soluble encapsulating film is desired, which releases the encapsulated material when the capsule is placed in contact with water. Other coatings are designed to release the entrapped material when the coating is ruptured by external force.

Still further coatings are porous in nature and release the entrapped material to the surrounding medium at a slow rate by diffusion through the pores. In addition to providing controlled release, such coatings also serve to facilitate the dispersion of water-immiscible liquids into water and water-containing media such as wet soil. Droplets encapsulated in this manner are particularly useful in agriculture, where water from irrigation, rain, and water sprays is frequently present. A variety of processes for producing such capsules is known.

In one process, the capsules are formed by phase separation from an aqueous solution through the coacervation of a hydrophilic colloid sol. This is described in U.S. Pat. Nos. 2,800,457 (Green et al., July 23, 1957) and 2,800,458 (Green, July 23, 1957).

An interfacial polymerization process is disclosed in U.S. Pat. Nos. 4,046,741 (Scher, Sept. 6, 1977) and 4,140,516 (Scher, Feb. 20, 1979), whereby the film-forming reactants are dissolved in the hydrophobic liquid which is dispersed in water, the reaction occurring at the interface when the phases are placed in contact as an emulsion.

A further interfacial polymerization process is described in U.S. Pat. No. 3,726,804 (Matsukawa et al., Apr. 10, 1973) whereby all the film-forming ingredients initially reside in hydrophobic droplets which also contain a low boiling or polar solvent in addition to the material to be encapsulated. Upon heating, the solvent is released into the aqueous phase (the continuous phase of the emulsion), and the film-forming materials accumulate at the interface and polymerize.

Olefin polymerization using a peroxide catalyst is described in Japanese patent publication No. 9168/1961, whereby an oil-insoluble polymer is formed at the surfaces of oil drops.

British Patent Nos. 952,807 and 965,074 describe a process whereby a solid such as wax or a thermoplastic resin is melted, dispersed and cooled to form an encapsulating film around liquid droplets.

U.S. Pat. No. 3,111,407 (Lindquist et al., Nov. 19, 1963) describes a spray drying method which forms encapsulated droplets at the instant of atomization.

These processes vary in terms of equipment expense, energy requirements, ease of controlling the microcapsule size, the need for extra reagents such as catalysts and settling agents, and percent microcapsule phase. It is therefore an object of the present invention to provide a simple, inexpensive method for producing microcapsules of uniform and readily controlled size, which are suitable for use without further treatment. Other objects of the invention will be apparent from the following description.

SUMMARY OF THE INVENTION

It has now been discovered that a liquid material which is substantially insoluble in water can be microencapsulated within a porous shell by a process which comprises:

(a) providing an organic solution comprising said material and an etherified urea-formaldehyde prepolymer dissolved therein in which from about 50% to about 98% of the methylol groups of said prepolymer have been etherified with a $C_4$–$C_{10}$ alcohol;

(b) creating an emulsion of said organic solution in an continuous phase aqueous solution comprising water and a surface-active agent, wherein said emulsion comprises discrete droplets of said organic solution dispersed in said continuous phase aqueous solution, there being formed thereby an interface between the discrete droplets of organic solution and the surrounding continuous phase aqueous solution; and (c) causing in situ self-condensation and curing of said ureaformaldehyde prepolymers in the organic phase of said discrete droplets adjacent to said interface by simultaneously heating said emulsion to a temperature between about 20° C. to about 100° C., and adding to said emulsion an acidifying agent and maintaining said emulsion at a pH of between about 0 to about 4 for a sufficient period of time to allow substantial completion of in situ condensation of said resin prepolymers to convert the liquid droplets of said organic solution to capsules consisting of solid permeable polymer shells enclosing said liquid material.

Microcapsules formed by this process are capable of effecting a slow rate of release of the encapsulated liquid by diffusion through the shell to the surrounding medium. The present invention resides in both the process described above and the microcapsules thus formed.

DESCRIPTION OF THE PREFERRED EMBODIMENTS

The present invention can be readily adapted to accomodate variations in the materials used, the kind of product desired, and economic factors in general. As the following indicates, both essential and optional features of the process and the product thereof can be varied over a wide range.

A. Core Liquid

It is essential that the organic solution which forms the interior of the capsules (i.e., the core liquid) be substantially insoluble in water. Preferably, its solubility under ambient conditions is approximately 5000 parts per million (ppm) by weight or less. The organic solution may consist of a single liquid material or one or more active liquid or solid materials dissolved in an inert solvent which has at most a slight solubility in water. In the latter case, the liquid or solid solute must reside preferentially in the organic phase when the two phases are in equilibrium.

A wide variety of liquids can be encapsulated by the present process. The most useful liquids are those which do not react with either the prepolymer, the acid used in the self-condensation wall-forming step, or any of the other components in the system. Thus, any nonreactive liquid which will diffuse through the shell membrane is suitable. The liquid can be a single chemical compound or a mixture of two or more compounds. It can diffuse into water, soil, air, or any other surrounding medium.

Liquids suitable for encapsulation include chemical-biological agents such as herbicides, insecticides, fungicides, nematocides, bactericides, rodenticides, molluscides, acaricides, larvicides, animal, insect, and bird repellents, plant growth regulators, fertilizers, pheromones, sex lures and attractants, and flavor and odor compositions. The microcapsules of the present invention are particularly well adapted to pesticides, including thiocarbamates, dithiocarbamates, acetamides, anilides, sulfonamides, triazines, organophosphorus compounds, and pyrethroids. The following are examples of such compounds, followed in parentheses by their common names where available:

HERBICIDES

S-ethyl-N-cyclohexyl-N-ethylthiocarbamate (cycloate)
S-ethyl hexahydro-1H-azepine-1-carbothioate (molinate)
S-2,3-dichloroallyl di-isopropylthiocarbamate (diallate)
S-2,3,3-trichloroallyl di-isopropylthiocarbamate (triallate)
S-ethyl dipropylthiocarbamate (EPTC)
S-4-chlorobenzyl diethylthiocarbamate (benthiocarb)
S-ethyl diisobutylthiocarbamate (butylate)
S-benzyl di-sec-butylthiocarbamate
S propyl dipropylthiocarbamate (vernolate)
S-propyl butylethylthiocarbaxate (pebulate)
N,N-diallylchloroacetamide (allidochlor)
α-chloro-6'-ethyl N-(2-methoxy-1-methylethyl)-acetanilide (metolachlor)
N-butoxymethyl-α-chloro-2',6'-diethylacetanilide (butachlor)
S-(O,O-diisopropyl phosphorodithioate) ester of N-(2-mercaptoethyl)benzenesulfonamide (bensulide)
N-benzyl N-isopropyltrimethylacetamide (butam)
2-chloroallyl diethyldithiocarbamate (CDEC)
2-sec-butyl-4,6-dinitrophenol (dinoseb)
2,6-dinitro-N,N-dipropylcumidine (isopropalin)
N-(cyclopropylmethyl)-α,α,-trifluoro-2,6-dinitro-N-propyl-p-toluidine (profluralin)
2-(1,2-dimethylpropylamino)-4-ethylamino-6-methylthio-1,3,5-triazine (dimethametryn)
2-ethyl 5-methyl-5-(2-methylbenzyloxy)-1,3-dioxane

INSECTICIDES

S-tert-butylthiomethyl O,O-diethyl phosphorodithioate (terbufos)
O,O-diethyl-O-4-methylsulphinylphenyl phosphorothioate (fensulfothion)
O,O-diethyl O-2-isopropyl-6-methylpyrimidin-4-yl phosphorothioate (diazinon)
O,O-diethyl S-2-ethylthioethyl phosphorodithioate (disulfoton)
S-chloromethyl O,O-diethyl phosphorodithioate (chlormephos)
O-ethyl S,S-dipropyl phosphorodithioate (ethoprophos)
O,O-diethyl S-ethylthiomethyl phosphorodithioate (phorate)
O-(4-bromo-2-chlorophenyl) O-ethyl S-propyl phosphorodithioate (prophenofos)
S-1,2-di(ethoxycarbonyl)ethyl O,O-dimethyl phosphorodithioate (malathion)
O,O,O',O'-tetraethyl S,S'-methylene di(phosphorodithioate) (ethion)
O-(4-bromo-2,5-dichlorophenyl) O,O-diethyl phosphorothioate (bromophosethyl)
S-4-chlorophenylthiomethyl O,O-diethyl phosphorodithioate (carbophenothion)
2-chloro-1-(2,4-dichlorophenyl)vinyl diethyl phosphate (chlorphenvinphos)
O-2,5-dichloro-4-(methylthio)phenyl O,O-diethyl phosphorodithioate (chlorthiophos)
O-4-cyanophenyl O,O-dimethyl phosphorothioate (cyanophos)
O,O-dimethyl O-2-methylthioethyl phosphorothioate (demephion)
O,O-diethyl O-2-ethylthioethyl phosphorothioate (demeton)
O-2,4-dichlorophenyl O,O-diethyl phosphorothioate (dichlorofenthion)
O-2,4-dichlorophenyl O-ethyl phenylphosphonothioate (EPBP)
O,O-diethyl O-5-phenylisoxazol-3-yl phosphorothioate (isoxathion)
1,3-di(methoxycarbonyl)-1 propen-2-yl dimethyl phosphate
S,S'-(1,4-dioxane-2,3-diyl) O,O,O'O'-tetraethyl di(phosphorodithioate) (dioxathion)
O,O-dimethyl-O-4-nitro-m-tolyl phosphorothioate (fenitrothion)
O,O-dimethyl O-4-methylthio-m-tolyl phosphorothioate (fenthion)
O-(5-chloro-1-isopropyl-1,2,4-triazol-3-yl) O,O-diethyl phosphorothioate (isazophos)
S-2-isopropylthioethyl O,O-dimethyl phosphorodithioate (isothioate)
4-(methylthio)phenyl dipropyl phosphate (propaphos)
1,2-dibromo-2,2-dichloroethyl dimethyl phosphate (naled)
O,O-diethyl α-cyanobenzylideneamino-oxyphosphonothioate (phoxim)
O,O-diethyl O-4-nitrophenyl phosphorothioate (parathion)
O-2-diethylamino-6-methylpyrimidin-4-yl O,O-diethyl phosphorothioate (pirimiphos-ethyl)
O-2-diethylamino-6-methylpyrimidin-4-yl O,O-dimethyl phosphorothioate (pirimiphos-methyl)
(E)-O-2-isopropoxycarbonyl-1-methylvinyl O-methyl ethylphosphoramidothioate (propetamphos)
O,O,O',O'-tetraethyldithiopyrophosphate (sulfotep)

O,O,O',O'-tetramethyl O,O'-thiodi-p-phenylene diphosphorothioate (temephos)

S-2-ethylthioethyl O,O-dimethyl phosphorodithioate (thiometon)

O,O-diethyl O-1-phenyl-1,2,4-triazol-3-yl phosphorothioate (triazophos)

O-ethyl O-2,4,5-trichlorophenyl ethylphosphonothioate (trichloronate)

(±)-3-allyl-2-methyl-4-oxocyclopent-2-enyl (+)-cis,-trans-chrysanthemate (allethrin)

(±)-3-allyl-2methyl-4-oxocyclopent-2-enyl (+)-trans-chrysanthemate (bioallethrin)

3-phenoxybenzyl (±)-cis,trans-chrysanthemate (phenothrin)

pyrethrins 2-(2-butoxyethoxy)ethyl thiocyanate isobornyl thiocyanoacetate (terpinyl thiocyanoacetate)

carbon disulfide 2-(4-tert-butylphenoxy)cyclohexyl prop-2-ynyl sulphite (propargite)

4,6-dinitro-6-octylphenyl crotonates (dinocap)

ethyl 4,4'-dichlorobenzilate (chlorobenzilate)

DEFOLIANTS

S,S,S-tributyl phosphorotrithioate tributyl phosphorotrithioite (merphos)

FUNGICIDES copper naphthenates 5-ethoxy-3-trichloromethyl-1,2,4-thiadiazole (etridiazole)

O-ethyl S,S-diphenyl phosphorodithioate (edifenphos)

INSECT REPELLENTS 6-butoxycarbonyl-2,3-dihydro-2,2-dimethylpyran-4-one (butopyronoxyl)

N,N-diethyl-m-toluamide (deet)

dibutyl phthalate dibutyl succinate 1,5a,6,9,9a,9b-hexahydro-4a(4H)-dibenzofurancarboxaldehyde dipropyl pyridine-2,5-dicarboxylate Of the many different types of core liquids useful in the present composition, pesticides are preferred, and certain classes of pesticides are particularly preferred. One such class is that of substituted thiocarbamates, particularly those of the formula

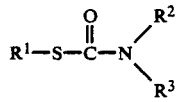

in which $R^1$ is selected from the group consisting of $C_1-C_6$ alkyl, $C_2-C_6$ alkenyl, and $C_7-C_9$ phenylalkyl, and is optionally substituted with up to three groups selected from halogen and nitro; and $R^2$ and $R^3$ are either independently $C_1-C_6$ alkyl or $C_5-C_7$ cycloalkyl, or conjointly form $C_4-C_7$ alkylene. The terms "alkyl," "alkenyl," and "alkylene" are intended to include both straight-chain and branched-chain groups, and all carbon atom ranges are intended to be inclusive of the upper and lower limits stated. More preferred thiocarbamates are those in which $R^1$ is $C_2-C_4$ alkyl and $R^2$ and $R^3$ either independently form $C_2-C_4$ alkyl or conjointly form hexamethylene. The most preferred are those in which $R^1$, $R^2$, and $R^3$ are all independently $C_2-C_4$ alkyl.

Thiocarbamates are particularly useful as preemergence and postemergence herbicides.

One can broaden the variety of crops on which certain pesticides, particularly herbicides, can be effectively used by including an antidote in the composition. The antidote helps to protect the crop from injury by the herbicide, without appreciable effect on the potency of the herbicide against the undesired weed species. The antidote thus renders the herbicide more selective in its action. Useful antidotes include acetamides such as N,N-diallyl-2,2-dichloroacetamide and N,N-diallyl-2-chloroacetamide, oxazolidines such as 2,2,5-trimethyl-N-dichloroacetyl oxazolidine and 2,2 spirocyclohexyl-N-dichloroacetyl oxazolidine, and 1,8-naphthalic anhydride. For maximum effect, the antidote is present in the composition in a non-phytotoxic, antidotally effective amount. By "non-phytotoxic" is meant an amount which causes at most minor injury to the crop. By "antidotally effective" is meant an amount which substantially decreases the extent of injury caused by the pesticide to the crop. The preferred weight ratio of pesticide to antidote is about 0.1:1 to about 30:1. The most preferred range for this ratio is about 3:1 to about 20:1.

The utility of many pesticides can also be broadened by the inclusion of synergists in the pesticide composition. Synergists are compounds which have little or no pesticidal activity of their own, but when combined with a pesticide produce a combination with a potency significantly greater than the additive sum of the potencies of the compounds applied individually. Useful synergists include 5- 1-[2-(2-ethoxyethoxy)ethoxy]ethoxy-1,3-benzodioxole (sesamex), 1,4-di-(1,3-benzodioxol-5-yl)tetrahydrofuro [3,4-c] furan (sesamin), 1-methyl-2-(3,4-methylenedioxyphenyl)ethyl octyl suphoxide (sulfoxide), and 5-[2-(2-butoxyethoxy)ethoxymethyl]-6propyl-1,3-benzodioxole (piperonyl butoxide). When included, synergists are present in effective amounts, i.e., at any pesticide to-synergist ratio at which a synergistic effect is observed. This ratio varies widely from one combination to the next.

B. Prepolymer

Prepolymers suitable to the present invention are partially etherified urea-formaldehyde prepolymers with a high solubility in the organic phase and a low solubility in water. In its non-etherified form, the prepolymer contains a large number of methylol groups, -CH$_2$OH, in its molecular structure. Etherification is the replacement of the hydroxyl hydrogens with alkyl groups, and is achieved by condensation of the prepolymer with an alcohol. When the alkyl groups comprise four carbon atoms or more and they have replaced more than about 50% of the hydroxyl hydrogen atoms on the prepolymer molecule, the prepolymer becomes soluble in the organic phase. Complete etherification is to be avoided, however, since hydroxyl groups are needed for the in situ self-condensation polymerization which occurs in the wall-forming step. Therefore, the prepolymers useful in the present invention are those in which from about 50% to about 98% of the hydroxyl hydrogen atoms have been replaced by alkyl groups of 4 to 10 carbon atoms each. In preferred practice, about 70% to about 90% of the groups have been etherified with a C$_4$-C$_6$ alcohol. Both straight-chain and branched-chain alcohols are useful in the present invention, and all carbon atom ranges quoted herein are to be inclusive of their upper and lower limits.

Etherified urea-formaldehyde prepolymers are commercially available as solutions in alcohol or in a mixture of alcohol and xylene. The alcohol used as the solvent is normally identical to that used as the etherifying agent. Those in most common use are n-butanol and iso-butanol. The degree of etherification (butylation) in these commercial products ranges between 70% and 90%, and the solution contains from 50% to 85% by weight of prepolymer. Minor amounts of free formaldehyde are also frequently present. These solutions are typically sold as cross-linking agents for alkyd resins and used primarily for the formulation of coating and finishing products such as paints and lacquers.

Urea-formaldehyde prepolymers which have not been etherified are also available commercially, either in aqueous solutions or as waterdissolvable solids, for use as adhesives. These can be etherified by condensation with the desired alcohol in a weakly acidic alcohol solution. The water of condensation is distilled off as an azeotrope with the alcohol until the desired degree of condensation (etherification) has been reached.

Urea-formaldehyde prepolymers themselves can be prepared by known techniques, notably the base-catalyzed reaction between urea and formaldehyde in water at a weight ratio of 0.6 to 1.3 parts formaldehyde to one part urea by weight (1.2:1 to 2.6:1 on a molar basis), at a pH of 7.5 to 11.0 and a temperature of 50° C. to 90° C. Etherification is then accomplished as described in the preceding paragraph.

The degree of etherification can be monitored by the quantity of water driven off during the distillation. Although the degree of etherification can be varied over a wide range to accommodate the needs of the reaction system, the rate of polymerization in the subsequent wall-forming step decreases as the degree of etherification increases. Too high a degree of etherification, therefore, tends to inhibit the progress of the wall formation. However, the water solubility of the prepolymer also decreases with increasing degree of etherification. Since low water solubility is a desirable feature of the prepolymer, it is best to avoid too low a degree of etherification. Thus, the suitable and preferred ranges are those stated above.

The organic solution comprising the core liquid and the etherified prepolymer is most conveniently formed when the latter is predissolved in a solvent, as it is when commercially sold for the coatings and finishings industry. In the absence of such a solvent, there is a high degree of hydrogen bonding between the hydroxyl groups, and the prepolymer is a waxy solid which is difficult to dissolve in the capsule core liquid. Polar organic solvents are particularly useful for preventing the hydrogen bonding and dissolving the prepolymer; examples include alcohols, ketones, esters, and aromatics. When etherifying agents of high chain length are used, aliphatics and other non-polar solvents can also be used. The most useful solvents are the same alcohols used as the etherifying agents, the solution being taken directly from the reaction mixture of the etherification process.

The concentration of the prepolymer in the organic phase is not critical to the practice of the invention, but can vary over a wide range depending on the desired capsule wall strength and the desired quantity of core liquid in the finished capsule. It will be most convenient, however, to use an organic phase with a prepolymer concentration of from about 1% to about 70% on a weight basis, preferably from about 5% to about 50%.

C. Optional Additives

Optional additives include solvents, polymerization catalysts, and wall-modifying agents.

Solvents provide a means for controlling the wall-forming reaction. As explained in Section E below, the reaction occurs when protons come in contact with the urea-formaldehyde prepolymer. The organic phase must be sufficiently hydrophilic to attract protons to the interface from the bulk of the aqueous phase, yet sufficiently hydrophobic to prevent large amounts of protons from crossing the interface and causing polymerization to occur throughout the bulk of the droplet. An appropriately selected solvent added to the organic phase can correct the character of the organic phase to achieve these results. Clearly, the need for a solvent and the type of solvent needed—hydrophobic or hydrophilic—depends on the nature of the liquid core material. Aliphatic and alicyclic solvents are examples of hydrophobic solvents, and alcohols and ketones are examples of hydrophilic solvents. The amount of solvent can be varied as needed to achieve the desired results.

Catalysts capable of enhancing the wall-forming reaction can be placed in either the aqueous or organic phase. Catalysts are generally used when the core material is too hydrophobic, since they serve to attract protons toward the organic phase. Any water-soluble catalyst which has a high affinity for the organic phase and is capable of carrying a proton can be used. Carboxylic and sulfonic acids are particularly useful. Examples include orthochlorobenzoic acid, 2-phenyl-2,2-dichloroacetic acid, benzoic acid, salicylic acid, p-toluenesulfonic acid and dodecylbenzene sulfonic acid. The same catalytic effect can be accomplished by dissolving salts of these acids in the aqueous or organic phase and then acidifying the aqueous phase. The acid form is produced by ion exchange.

Wall-modifying agents serve to modify the character of the wall by varying its permeability to the core material. Suitable wall-modifying agents contain a substantial number of hydroxyl or mercapto groups capable of reacting with the methylol groups on the prepolymer. The wall modifier can be used in the organic solution to add multiple linkages to the methylol groups to increase the degree of cross-linking, or to exhaust active sites on the prepolymer to decrease the degree of cross-linking. Thus, depending on the kind of modifier used and the ratio of modifier to prepolymer, the permeability of the wall (and consequently the release rate of the core liquid) can be either increased or decreased. Castor oil is one example of such an agent. The preferred cross-linking wall-modifying agent is pentaerythritol tetrakis (mercaptopropionate) sold under the tradename Mercaptate Q-43 Ester, by Cincinnati Milacron Chemicals. Other poly-functional mercaptan esters of a similar nature can be used.

D. Emulsion Formation

Once the organic solution is formed, an emulsion is formed by dispersing the organic solution in an aqueous solution comprising water and a surface-active agent. The relative quantities of organic and aqueous phase are not critical to the practice of the invention, and can vary over a wide range, limited mostly by convenience and ease of handling. In practical usage, the organic phase will comprise a maximum of about 55% by volume of the total emulsion and will comprise discrete droplets of organic solution dispersed in the aqueous solution.

The surface-active agent can be any of the wide variety of compounds known to be useful for lowering the surface tension of a fluid interface. Nonionic and anionic types are both useful. Examples of nonionic agents are long chain alkyl and mercaptan polyethoxy alcohols, alkylaryl polyethoxy alcohols, alkylaryl polyether alcohols, alkyl polyether alcohols, polyoxyethylene sorbitan fatty acid esters, polyoxyethylene ethers, and polyethylene glycol esters with fatty or rosin acids. Examples of anionic agents are the calcium, amine,, alkanolamine, and alkali salts of alkyl and alkylaryl sulfonates; vegetable sulfonates; and ethoxylated and propoxylated mono- and diethers of phosphoric acid. Blends of surface-active agents are also useful. Preferred surface-active agents are polyethelene glycol ethers of linear alcohols and alkali salts of alkyl and alkylaryl sulfonates.

The quantity of surface-active agent is not critical to the invention, and can vary over a wide range. For convenience, the agent generally comprises from about 0.1% to about 5.0% by weight of the aqueous phase. The agent can be added before or after the emulsion is formed.

In some systems, emulsion stability can be enhanced by adding a protective colloid to the aqueous phase. A protective colloid stabilizes a dispersed system against aggregation, flocculation, and coalescense. Many materials are known to function as protective colloids and are available commercially, including polyvinyl alcohols, alginates, alpha- and gamma protein, casein, methyl cellulose, carboxymethyl cellulose, gelatin, glues, natural gums, polyacids, and starch. The colloid can be added to the aqueous phase prior to the formation of the emulsion, or to the emulsion itself after it has been formed. Although the colloid is an optional additive, its inclusion in the present system is preferred. Polyvinyl alcohol protective colloids are particularly preferred.

Additional compounds which serve as protective colloids are the salts of lignin sulfonate, such as the sodium, potassium, magnesium, calcium or ammonium salts. Among commercial lignin sulfonates are Treax ®, LTS, LTK and LTM, respectively, the potassium, magnesium and sodium salts of lignosulfonate (50% aqueous solutions), Scott Paper Co., Forest Chemical Products; Marasperse CR ® and Marasperse CBOS-3 ®, sodium lignosulfonate, American Can Co.; Polyfon O ®, Polyfon T ®, Reax 88B ®, Reax 85B ®, sodium salts of lignin sulfonate and Reax C-21 ®, calcium salt of lignin sulfonate, Westvaco Polychemicals; Orzan S and Orzan A, the sodium and ammonium salts of lignosulfonate, ITT Rayonier, Inc.

The actual quantity of colloid is not critical and any amount which is effective in enhancing the stability of the emulsion can be used. It is most convenient to use between about 0.1% and about 5.0% colloid by weight in terms of the aqueous phase.

The droplet size in the emulsion is not critical to the invention. For greatest utility of the final product, the droplet size will fall in the range of about 0.5 microns to about 4000 microns in diameter. The preferred range for most pesticidal applications is from about 1 micron to about 100 microns in diameter. The emulsion is prepared by the use of any conventional high shear stirring device. Once the desired droplet size is attained, mild agitation is generally sufficient to prevent droplet growth throughout the balance of the process.

E. Wall Formation

Once the dispersion and desired droplet size are attained, the system is acidified to a pH of between about 0 and about 4.0, preferably between about 1.0 and about 3.0. This causes the etherified urea-formaldehyde prepolymer to polymerize by self-condensing in situ and from a shell completely enclosing each droplet. Acidification can be accomplished by any suitable means, including adding any acid which is water-soluble, including formic acid, citric acid, hydrochloric acid, sulfuric acid, phosphoric acid, and the like. Acidification can also be achieved by the use of acidic dispersants or surface-active agents, provided that such components are added to the system after the emulsion has been formed.

As the polymer wall becomes more rigid, contact between the active groups on the prepolymer becomes increasingly more difficult. Thus, the in situ self-condensation polymerization reaction is self-terminating and is generally allowed to run to completion. The reaction can be arrested before completion, however, by raising the pH. In this manner, the wall tightness, rigidity, and permeability can be controlled. This can also be accomplished in most cases by a wall modifier as described above.

The rate of the in situ self-condensation polymerization reaction increases with both acidity and temperature depending upon the pH. The reaction can therefore be conducted anywhere within the range of about 20° C. to about 100° C., preferably between about 40° C. and about 70° C. The reaction will generally be complete within a few hours, although with high acidity and high temperature, the reaction can be completed within minutes.

Once the capsules are formed, they can be stored and used as an aqueous dispersion, or filtered and recovered as dried capsules. In either form, the capsules are useful and effective in the slow release of the core liquid. Dispersions are preferably stabilized by dispersants dissolved in the continuous phase. Since most dispersants are more effective in neutral or basic solutions, it is preferable to raise the pH of the dispersion once the wall has been formed. This is accomplished by any water-soluble base. Any conventional dispersant can be used. Typical dispersants include lignin sulfonates, polymeric alkylnaphthalene sulfonates, sodium naphthalene sulfonate, polymethylene bis-naphthalene sulfonate, and sodiumN-methyl N-(long chain acid) taurates.

A unique feature of the process of the invention is that the solid permeable polymer shells enclosing the organic phase droplets are formed by means of condensation of the urea-formaldehyde prepolymer in the organic phase adjacent to the interface formed between the organic phase droplets and the aqueous phase solution. This is a consequence of the urea-formaldehyde prepolymers being dissolved in the organic phase The advantages of forming the polymer shells on the organic side of the interface are several. The first is that the process itself is more easily controlled than the prior art processes, which involve wall-forming condensation in the aqueous phase. When the condensation takes place in the aqueous phase, the wall-forming polymer can deposit upon the walls of the container in which the emulsion is present, on the agitator or any other structure which may be present, in addition to depositing on the droplets. In contrast, the wall-forming polymer that condenses on the organic side of the interface does not deposit on any of the container walls or other structures.

Additionally, when the condensation takes place in the aqueous phase, as in the prior art, a reduced amount of dispersed organic phase must be used inasmuch as if a higher dispersed organic phase content is utilized, the dispersion gets too thick and gels, thus effectively preventing formation of the microcapsules. Condensation on the organic side of the interface thus allows higher dispersed organic phase loading to be obtained because a gel is not formed in the aqueous phase.

In the examples set forth herein, in which the organic phase contains a pesticide, a higher loading of organic phase results in a more concentrated pesticide formulation. This enables substantial cost savings to be achieved in manufacturing, packaging and transportation.

The following examples are offered as illustrative of both the process and product of the present invention, and are intended neither to define nor limit the invention in any manner.

EXAMPLE 1

An aqueous solution was prepared, comprising 2.0% (weight) Gelvatol ® 40-20 and 0.3% Tergitol ® 15-S-7, with a total solution weight of 300 g. Gelvatol 40-20 is a polyvinyl alcohol protective colloid (degree of hydrolysis 73–77%), with an average molecular weight of about 3000, obtained from Monsanto Company, Indian Orchard, Mass. Tergitol 15-S-7 is a nonionic surfactant consisting of a polyethylene glycol ether of a linear alcohol, obtained from Union Carbide Chemicals and Plastics Company, New York, N.Y.

In a separate vessel, 100 g of S-ethyl diisobutylthiocarbamate (a herbicide known by the common name "butylate") and 50 g of Beckamine ® 21-625 were blended into a homogeneous solution. Beckamine 21-625 is a 70–75% n-butanol solution of a partially butylated ureaformaldehyde prepolymer in which the degree of butylation is approximately 80–90%, obtained from Reichhold Chemicals, Inc., White Plains, N.Y.

The thiocarbamate/prepolymer (organic) solution was added to the aqueous solution and an emulsion was formed by means of a high shear stirrer, the organic solution forming the dispersed phase with droplets ranging in size from 5 to 40 microns in diameter. While mild agitation was maintained, the pH of the emulsion was adjusted to 2.0 with concentrated hydrochloric acid and the temperature was raised to 50° C. for three hours. The resulting suspension was then allowed to cool to room temperature and concentrated aqueous sodium hydroxide was added to raise the pH to 7.0.

Observation of the suspension under both a laboratory microscope and an electron microscope revealed discrete, roughly spherical, fully enclosed capsules with smooth-surfaced outer walls. The capsules were about 5 to 40 microns in diameter and although some were touching each other, none were fused together.

EXAMPLE 2

An organic solution was prepared, comprising 162.2 g of 2-methoxy-9-(p-isopropylphenyl)-2,6-dimethylnonane (a known insect maturation inhibitor—see U.S. Pat. No. 4,002,769, issued Jan. 11, 1977, to Schwarz et al.) and 48.0 g of Resimene ® X-918. The latter is a 70% n-butanol solution of a partially butylated ureafonmaldehyde prepolymer with a degree of butylation of approximately 80–90%, a product of Monsanto Plastics and Resins Company, Newport Beach, Calif.

This solution was added to an aqueous solution comprising 168.1 g of water and 1.87 g of Gelvatol 40-20 and an emulsion was formed as in Example 1, with droplets ranging in diameter from 1 to 40 microns. To this emulsion was added 20 g of water containing 1.87 g each of the dispersants Lomar NCO ® and Darvan ® #2. The former is a product of Diamond Shamrock Chemical Company, Nopco Division, Morristown, N.J., and is a sodium salt of a condensed mononaphthalene sulfonic acid. The latter is a product of R. T. Vanderbilt Company, Inc., Norwalk, Conn., and is comprised of sodium salts of polymerized substituted benzoic alkyl sulfonic acids. A 5% hydrochloric acid solution was added to lower the pH of the emulsion to 2.0 and the temperature was raised to 50° C. with continued stirring for three hours. The resulting dispersion was then cooled to room temperature and concentrated caustic solution was added to raise the pH to 9.0.

Microscopic observation of the dispersion revealed fully formed, discrete capsules as in Example 1.

EXAMPLE 3

The organic solution for this example consisted of 139.9 g of O-ethyl S-phenyl ethylphosphonodithioate (a commercial insecticide also known by the common name "fonofos") and 39.9 g of Resimene X-918. This solution was emulsified in an aqueous solution consisting of 200 g of water and 2.35 g of Gelvatol 40-20 to a droplet size of 1 to 40 microns, and 35 g of water containing 2.35 g each of the dispersants Lomar NCO and Darvan #2, as well as 2.4 g of p-toluene sulfonic acid, was added. The temperature was raised to 60° C. and stirring was continued for three hours. The dispersion was then allowed to cool to room temperature and the pH was raised to 9.0 with caustic solution.

Microscopic observation of the dispersion revealed fully formed, discrete capsules as in Example 1.

EXAMPLE 4

The organic solution for this example consisted of 156 g of HI-SOL ® 4-3 and 43.5 g of Beckamine 21-625. The former is a heavy aromatic naphtha, with boiling temperature ranging from 238° C. to 286° C., a product of Ashland Chemical Company, Industrial Chemicals and Solvents Division, Columbus, Ohio. This solution was emulsified in an aqueous solution consisting of 194.6 g of water, 3.9 g of Gelvatol 40-20, and 7.8 g of Darvan #2, to a droplet size of 1 to 40 microns. The pH was adjusted to 2.0 with a 5% solution of hydrochloric acid and the temperature was raised to 50° C. with continued stirring for three hours. The dispersion was then allowed to cool to room temperature and the pH was raised to 9.0 with caustic solution.

Microscopic observation revealed fully formed, discrete capsules as in Example 1.

EXAMPLE 5

An aqueous solution consisting of 251.6 g of water, 5 g of Gelvatol 40-20, and 2.5 g of Tamol ® SN was heated to 50° C. Tamol SN is a dispersant identified as a sodium salt of a condensed naphthalene sulfonic acid, obtained from Rohm and Haas Company, Philadelphia, Pa. To this heated aqueous solution was added an organic solution consisting of 173.4 g of S-ethyl diisobutylthiocarbamate (butylate), 7.5 g of N,N-diallyl dichloroacetamide, and 22.5 g of Resimene X-918. The thiocarbamate/ acetamide combination is a known herbicide/antidote combination—see U.S. Pat. No. 4,021,224, issued May 3, 1977, to Pallos et al. An emulsion was formed by means of a high-speed stirrer as in the above examples, to a droplet size of 1 to 40 microns. The high temperature was maintained and the pH was lowered to 2.0 with 5% hydrochoric acid. After three hours of additional stirring, the dispersion was cooled to room temperature and the pH was raised to 9.0 with caustic solution.

Microscopic observation revealed fully formed, discrete capsules as in Example 1.

EXAMPLE 6

In this example, an additional feature is demonstrated—the inclusion of an organic solvent (kerosene) in the organic phase, the solvent thus becoming part of the encapsulated liquid.

The aqueous solution was prepared with 177.12 g of water, 2 g of Gelvatol 40-20, and 2 g of Darvan #2. The organic solution was prepared with 132.74 g of S-ethyl hexahydro-1H-azepine-1-carbothioate (a commercial herbicide known by the common name "molinate"), 44.25 g of kerosene, and 35.48 g of Beetle ® 1050-10. The latter is a 60% n-butanol solution of a partially butylated urea-formaldehyde prepolymer in which the degree of butylation is approximately 70-90%, obtained from American Cyanamide Company, Resins Department, Wayne, N.J.

The organic solution was emulsified in the aqueous solution by means of a high shear stirrer to an average droplet diameter of 18 microns, and 19.68 g of water containing 2 g of DAXAD ® LAA was slowly added, lowering the pH of the emulsion to 1.7. DAXAD LAA is a dispersant in acidic from, identified as a polymerized alkyl naphthalene sulfonic acid, a product of W. R. Grace and Company, Organic Chemicals Division, Lexington, Mass.

The emulsion temperature was then raised to 50° C. for three hours with continued stirring. The dispersion thus formed was cooled to room temperature and the pH was raised to 7.5 with caustic solution.

Microscopic observation revealed fully formed, discrete capsules as in Example 1.

EXAMPLE 7

In this example, two additional features are demonstrated—the inclusion of kerosene as in Example 6 and the addition of a wall-modifying component (castor oil) to the prepolymer.

The aqueous solution was prepared with 181.6 g of water, 2 g of Gelvatol 40-20, and 2 g of Darvan #2. The organic solution was prepared with 132.7 g of S-ethyl hexahydro-1H-azepine-1-carbothioate, 44.25 g of kerosene, 22.97 g of Beetle 1050-10, and 6.9 g of castor oil. An emulsion with an average droplet diameter of 18 microns was formed, and 20.2 g of water containing 2 g of DAXAD LAA was added, lowering the pH to 1.7. The emulsion temperature was then raised to 50° C. for three hours with continued stirring. The resulting dispersion was then cooled to room temperature and the pH was raised to 7.5 with caustic solution.

Microscopic observation revealed fully formed, discrete capsules as in Example 1.

EXAMPLE 8

This example demonstrates microcapsule preparation according to the present invention without the use of a protective colloid.

The organic solution consisted of 154 g of butylate, 6.7 g of N,N-diallyl dichloroacetamide, and 47.6 g of Resimene X-918 (same ingredients as Example 5). This solution was emulsified in 197.8 g of a 4.0% (by weight) aqueous solution of Darvan #2 to a droplet size of 1 to 40 microns. The pH of the dispersion was then adjusted to 2.0 with a 5% solution of hydrochloric acid and the temperature was raised to 50° C. with continuous stirring for three hours. The dispersion was then allowed to cool to room temperature and the pH was raised to 9.0 with caustic solution.

Microscopic observation of the dispersion revealed fully formed, discrete capsules as in Example 1.

What is claimed is:

1. A process for the microencapsulation of a substantially water-insoluble liquid material within a porous shell to effect a slow rate of release of said material through said shell which comprises
    (a) providing an organic solution comprising said liquid material and an etherified urea-fonmaldehyde prepolymer dissolved therein in which from about 50% to about 98% of the methylol groups of said prepolymer have been etherified with a $C_4$–$C_{10}$ alcohol;
    (b) creating an emulsion of said organic solution in an continuous phase aqueous solution comprising water and a surface-active agent, wherein said emulsion comprises discrete droplets of said organic solution dispersed in said continuous phase aqueous solution, there being formed thereby an interface between the discrete droplets of organic solution and the surrounding continuous phase aqueous solution; and
    (c) causing in situ self-condensation and curing of said ureaformaldehyde prepolymers in the organic phase of said discrete droplets adjacent to said interface by simultaneously heating said emulsion to a temperature between about 20° C. to about 100° C., and adding to said emulsion an acidifying agent and maintaining said emulsion at a pH of between about 0 to about 4 for a sufficient period of time to allow substantial completion of in situ condensation of said resin prepolymers to convert the liquid droplets of said organic solution to capsules consisting of solid permeable polymer shells enclosing said liquid material.

2. A process according to claim 1 in which from about 70% to about 90% of the methylol groups of the prepolymer of step (a) have been etherified.

3. A process according to claim 1 in which the alcohol with which the methylol groups of the prepolymer of step (a) have been etherified is a $C_4$–$C_6$ alcohol.

4. A process according to claim 1 in which the alcohol with which the methylol groups of the prepolymer of step (a) have been etherified is n-butanol or isobutanol.

5. A process according to claim 1 in which from about 70% to about 90% of the methylol groups of the prepolymer of step (a) have been etherified and the alcohol with which said methylol groups have been etherified is n-butanol.

6. A process according to claim 1 in which, prior to the formation of the organic solution of step (a), the prepolymer of step (a) is dissolved in an alcohol which is identical to that with which the prepolymer has been etherified.

7. A process according to claim 1 in which the surface active agent of step (b) is selected from the group consisting alkali salts of alkyl and alkylaryl sulfonates.

8. A process according to claim 1 in which the aqueous solution of step (b) further comprises a protective colloid.

9. A process according to claim 1 in which the aqueous solution of step (b) further comprises from about 0.1% to about 5.0% by weight of a polyvinyl alcohol protective colloid.

10. A process according to claim 1, 2, 3, 4, 5, 6, 7, 8, or 9 in which the prepolymer of step (a) comprises from about 1% to about 70% of the organic solution on a weight basis.

11. A process according to claim 1, 2, 3, 4, 5, 6, 7, 8, or 9 in which the prepolymer of step (a) comprises from about 5% to about 50% of the organic solution on a weight basis.

12. A process according to claim 1, 2, 3, 4, 5, 6, 7, 8, or 9 in which the protective colloid of step (b) is a polyvinyl alcohol and comprises from about 0.1% to about 5.0% by weight of the aqueous phase.

13. A process according to claim 1, 2, 3, 4, 5, 6, 7, 8, or 9 in which the droplets of the dispersion formed in step (b) are from about 0.5 microns to about 4000 microns in diameter.

14. A process according to claim 1, 2, 3, 4, 5, 6, 7, 8, or 9 in which the droplets of the dispersion formed in step (b) are from about 1 micron to about 100 microns in diameter.

15. A process according to claim 1, 2, 3, 4, 5, 6, 7, 8, or 9 in which the in situ self-condensation in step (c) is done at a pH of between about 1.0 and about 3.0.

16. A process according to claim 1, 2, 3, 4, 5, 6, 7, 8, or 9 in which the in situ self-condensation in step (c) is done at a pH of between about 1.0 and about 3.0 and at a temperature between about 40° C. and about 70° C.

17. A process according to claim 1 wherein said organic solution contains a wall-modifying agent which serves to modify the character of the wall by varying its permeability to the core material.

18. A process according to claim 17 wherein said wall-modifying agent is pentaerythritol tetrakis (mercaptopropionate).

* * * * *